United States Patent [19]

Brauman

[11] Patent Number: 4,963,150
[45] Date of Patent: Oct. 16, 1990

[54] IMPLANTABLE PROSTHETIC DEVICES

[76] Inventor: Daniel Brauman, 141 Brush Hollow Cresent, Rye Brook, N.Y. 10572

[21] Appl. No.: 319,019

[22] Filed: Mar. 6, 1989

Related U.S. Application Data

[60] Continuation of Ser. No. 12,583, Feb. 9, 1987, which is a division of Ser. No. 630,124, Aug. 30, 1984, Pat. No. 4,648,880.

[51] Int. Cl.$^5$ ................................................ A61F 2/12
[52] U.S. Cl. ........................................... 623/8; 623/11
[58] Field of Search ................................. 623/7, 8, 12; 128/DIG. 21

[56] References Cited

PUBLICATIONS

McGhan, "Intrashield Mammary Implant" Medical brochure of McGhan Med. Corp. Santa Barbara, CA, Apr. 1980.
Picha & Siedlak, "Ion–Beam Microtexturing of Biomaterials" Med. Dev. & D.I., vol. 6, No. 4 (Apr. 1984) pp. 39–42.
Barton, Jr., "Augmentation Mammaplasty" Selected Readings in Plastic Surgery, vol. 3, No. 29 (Dec. 1985) pp. 1–17.
Taylor & Gibbons, "Effect of Surface Texture . . . ." Jr of Biomedical Materials Research, vol. 17, (1983), pp. 205–207, John Wiley & Sons.

Primary Examiner—David J. Isabella
Attorney, Agent, or Firm—Lawrence Rosen

[57] ABSTRACT

An improved implantable prosthetic device for use in the human body which comprises a flexible container having therein a soft gel or fluid filling and an outer plastic covering bonded or otherwise connected to the flexible container. The external surface of the outer plastic covering is rough textured, while the plastic covering itself has numerous pores or interstices. It substantially encases the flexible container. In one embodiment a barrier film is positioned between the flexible container and the outer plastic covering or between the soft gel or liquid filling and the internal of the flexible container. The outer plastic covering is made of Dacron or Teflon.

4 Claims, 1 Drawing Sheet

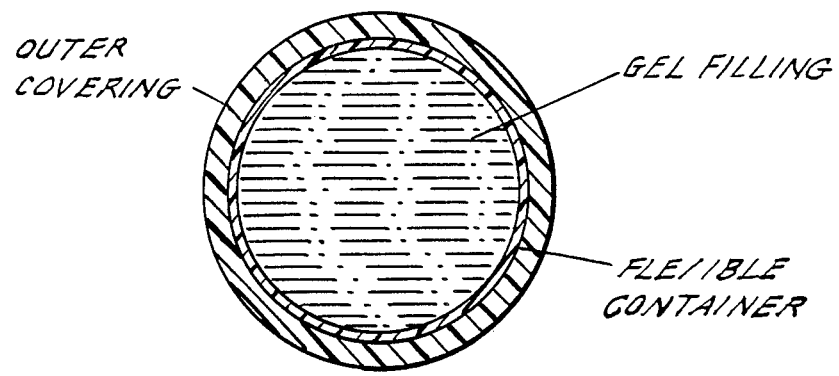
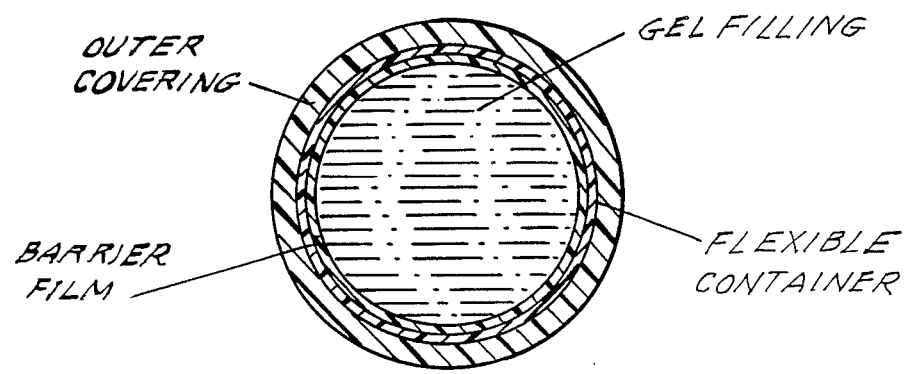

IMPLANTABLE PROSTHETIC DEVICES

CROSS REFERENCE TO RELATED APPLICATIONS

This application is a continuation of U.S. patent application Ser. No. 12,583, filed Feb. 9, 1987, which was a divisional of earlier filed U.S. patent application Ser. No. 630,124, filed Aug. 30, 1984, now U.S. Pat. 4,648,880.

FIELD OF THE INVENTION

The present invention relates to improved implantable prostheses which resist spherical capsular contracture. More particularly, the invention pertains to improved prosthetic devices for rescoring or improving normal body contour or augmenting as well as reconstructing the female breast. It may also be used to augment or reconstructing tissue on various locations on the human body.

BACKGROUND OF THE INVENTION

In recent years one of the most popular implantable procedures was a gel-filled silicon bag. This prosthesis has been employed for a number of years for breat augmentation and reconstruction. In U.S. Pat. 3,293,663 to Cronin, the breast prosthesis comprises (1) a flexible container approximating the shape of the human breast, (2) a soft gel filling said container, and (3) a layer of porous material attached to one side of said container so that the tissue can grow into said porous material to another the prosthesis to the chest wall.

U.S. Pat. 4,205,401 to Frisch and 4,264,990 to Hamas reveals that when a Cronin-type of prosthesis is implanted after a certain period of time the prosthesis is surrounded by a natural capsule composed of fibrous scar tissue. Although this is a normal tissue reaction to the presence of a foreign body, it has the disadvantage in that the scar may undergo contraction during the healing process. This effect, which is known as the sperical contracture of the prosthesis, leads to a relatively rigid and tense structure. More specifically, as the tissue around the implant contracts the fixed volume of the silicon gel and material within the flexible container is forced into a shape having the smallest possible surface area, i.e. a sphere surrounded by essentially scar tissue. As pointed as by Frisch, the resulting hard spherical prosthesis results in an aesthically undesirable breast.

Both the Frisch and Hamas disclose various prior art efforts to overcome the sperical capsular contracture problem. Disadvantages of the piror art suggestions are also discussed by the patentees. Frisch's invention is to resist capsular contracture by employing a flexible container which has structural restraining means positioned within the container or the container walls which function to restrain the scar tissue pressure. On the other hand, Hamas proposes the use of a special flexible backing of an inert polymeric material which defines passageways and/or compartments into which a second material may be injected or already placed to rigidfy the backing. This is somewhat of an attempted improvement over the Cronin device which uses a back porous layer such as a Dacron fabric. There are many other proposed suggestions, but they were also found to have disadvantages and flaws.

Thus, the devices heretofore proposed for overcoming the capsular contracture problem have not been found to be effective. It is also very important that the implant can be readily removed in its entirety from the human body in the even that an infection or undesirable reaction to the implant occurs or should total repositioning or total removal be desired for whatever reason.

SUMMARY OF THE INVENTION

The present invention is directed to improved implantable prosthesis for use in the human body comprising a flexible container with a soft gel or fluid filling and an outer plastic or polymeric covering bonded to the flaxible container and substantially encompassing said container. The outer plastic polymeric covering is made from Dacron or Teflcn and has numerous pores or interstices as well as a rough textured external surface. It is also possible to employ a barrier film or membrane disposed between the flexible container and the outer covering or positioned within the flexible container.

One object of the present invention to provide an implantable prosthesis whichg will disperse or disorganize the force of encapsulating tissue sufficient to avoid formation of a spherical capsular contracture.

Another object of the present invention is to provide an implantable prosthesis which can readily be removed in its entirety, if desired, from the human body without encountering any untoward affects.

A further object of the present invention is to provide an improved mammary prosthesis which avoids or substantially decreases the formation of a spherical capsular contracture.

BRIEF DESCRIPTION OF THE DRAWINGS

The above objects and advantages of the present invention will be more fully understood by reference to the following description and to the annexed drawing, in which:

FIG. 1 shows an implantable breast prosthesis having a soft gel filling a flexible container and an outer covering with a rough textured external surface.

FIG. 2 shows an implantable breast prosthesis having a soft gel filling, a barrier film, a flexible container, and an outer covering with a rough textured external surface.

DETAILED DESCRIPTION OF THE INVENTION

The invention will be described more specifically with respect to a mammary proshesis including a flexible container, envelope, or sac filled with a gel or any of the other conventional materials utilized in this art. The fiexible container is formed of a flexible silicon rubber or Silastic membrane and the gel, for example, is a semifluid silicone or liquid methylsiloxane resin capable of having a consistency which will provide resiliency and maintain the proper contour of the container. As known in the art, any suitable materials which do not cause tissue reaction and which are soft and flexible can be utilized for these purposes. For the present purposes, however, the preferred material for the flexible material is silicon rubber while the preferred gel is a silicon gel. Such material will often exhibit an elastic memory. The disclosure in column 2, line 32–46, of U.S. Pat. 3,293,663 is incorporated herein by reference with respect to the gel material that can be employed.

The container itself may be formed of a physiological inert elastomeric material which includes a number of known plastics. As previously stated, the use of silicon rubber is preferred, but for certain purposes organic rubbers made from butyl polymer or the natural polymer from the Hevea tree could be effectively employed. The use of dimethylsiloxane polymer to form the flexible container is also encompassed.

The thickness of the container wall will generally range from about 0.025 to 0.5 millimeters, but it can vary widely. In general, the flexible container is filled with a silicon gel or, if desired, with the saline solutions which have been recently proposed for this purpose, in amounts sufficiant to give the prosthesis a pliant, responsive nature as well as the desired profile.

A conventional barrier, film or membrane may be bonded laminated or adhesively connected to the internal or external wall of the flexible container to eliminate any seepage of the filler material out of the wall of the flexible container. It may be made of materials such as a vinylidene fluoridehexafluoropropylene-based fluororubber as disclosed in U.S. Pat. 4,413,359.

The essential feature of the present invention is the use of an outer plastic or polymeric covering for the flexible bag or the flexible bag provided with a barrier film or membrane. Thus, the nature of the flexible container, the material used to fill it, and the barrier film are less important than the external surface of the plastic or polymeric covering as well as its nature. In order to overcome the spherical capsular contracture discussed above, the external or outer surface of the polymeric film or plastic film has to be rough textured as well as being able to permit tissue ingrowth. Thus, the rough texture of the external surface, which will have pores or interstices, will break up the orderly alignment of the collagen fibers in the scar or fibrous capsule surrounding the implanted prostesis. Although at this time it is not fully understood how this outer covering with the special external surface functions, it is believed that it is the orderly alignment of the collagen in the fibrous capsules around the smooth prosthesis implant which cause spherical capsular contraction. In the present invention this orderly alignment is disrupted or disorganized.

In accordance with another feature of the present invention it has been found that despite the rough textured external surface of the outer convering the implant can be completely removed without any problems in the event of an infection or otherwise indicated or undesired.

The preferred material for use as the outer covering is polyester fibers such as Dacron which is a polymerized ethylene glycol terephthalate. Although the polyester fiber may be woven, knitted, braided or formed into felt; the use of knitted polyester fiber is found to be superior because it provides more elasticity and tissue in growth. Knitted Dacron velour is the especially preferred material, since the velour structure may further assist in disrupting or disorganizing the orderly alignment of the collagen fibers. It may be crimped to additional elasticity.

In accordance with another feature of this invention it has been found that tetrafluoroethylene polymer such as Teflon, can also be utilized for the purposes of preparing an improved implantable prosthesis which will resist spherical capsular contracture. The polymeric material is most useful when it is employed in its expanded from. Such an expanded Teflon is sold commercially under the name Gortex.

The outer covering will of course be bonded, laminated or adhesively secured to the flexible container or to the outer surface of the intermediate barrier film when the latter is employed in this position. The thickness of the outer covering and may vary over a wide range. Thus, for example, it may have a thickness of from about 0.01 to 1 millimeter. By a "rough textured" outer surface it is meant that the external surface of the outer covering will, by its nature, have numerous pores and/or interstices. If velour is used, fibers will project out from the external surface of the covering. Both the size and number of the pores and interstices may vary, but it is important that substantial pores and/or interstices be present in order to obtain the desired benefit of the present invention.

Although the invention has been described above with respect to certain of its more important features, it will be understood that the invention is subject to variations and modifications without departing from its broader scope. Thus, for example, in addition to mammary prosthesis the improved implantable devices of this invention can also be used for different shapes and forms for the purpose of augmenting tissue anywhere on the animal or human body for aestetic and reconstructive purposes. Augmentation of tissue include augmentation of hypoplastic or missing tissure for reconstructive purposes as well as the augmentation of tissue for aesthetic purposes. It is also possible, for example, to use silicone foam or a rough textured silicon envelope as the external covering, but at the present time they are not preferred materials for the present purposes.

What is claimed is:

1. In an implantable prosthetic device for use in a human body including a flexible container and a soft gel or liquid filling the flexible container;
   the improvement which comprises providing an outer plastic covering made of rough textured silicone and bonded to the flexible container, said outer plastic convering having a rough textured external surface thereby providing a multiplicity of pores and/or interstices, said outer plastic covering encases the flexible container in order to prevent the contraction of scar tissue around the prosthetic device from pulling the prosthetic device into a hard, spherical shape.

2. In the implantable prosthetic device of claim 1 wherein a barrier film is positioned between the flexible container and the outer plastic covering having said rough, textured external surface or inside the flexible container.

3. In the implantable prosthetic device of claim 2 wherein said barrier film is a fluororubber.

4. In a breast prosthesis comprising a flexible container approximating the shape of the human breast and a soft gel or liquid filling said container;
   the improvement which comprises providing an outer, rough textured plastic covering made of rough textured silicone and which encases the flexible container and has an outer surface having a multiplicity of pores and/or interstices.

* * * * *

REEXAMINATION CERTIFICATE (2407th)
United States Patent [19]
Brauman

[11] B1 4,963,150
[45] Certificate Issued Oct. 4, 1994

[54] IMPLANTABLE PROSTHETIC DEVICE

[76] Inventor: Daniel Brauman, 141 Brush Hollow Cresent, Rye Brook, N.Y. 10572

Reexamination Request:
No. 90/002,659, Mar. 2, 1992

Reexamination Certificate for:
Patent No.: 4,963,150
Issued: Oct. 16, 1990
Appl. No.: 319,019
Filed: Mar. 6, 1989

Related U.S. Application Data

[60] Continuation of Ser. No. 12,583, Feb. 9, 1987, which is a division of Ser. No. 630,124, Aug. 30, 1984, Pat. No. 4,648,880.

[51] Int. Cl.$^5$ ............................................. A61F 2/12
[52] U.S. Cl. ................................................ 623/8; 623/11
[58] Field of Search ........................... 623/7, 8, 11, 12

[56] References Cited

U.S. PATENT DOCUMENTS

| | | | |
|---|---|---|---|
| 3,189,921 | 6/1965 | Pangman | 623/8 |
| 3,293,663 | 12/1966 | Cronin | 623/8 |
| 3,366,975 | 2/1968 | Pangman | 623/8 |
| 3,559,214 | 2/1971 | Pangman | 623/8 |
| 3,600,718 | 8/1971 | Boone | 623/8 |
| 3,683,424 | 8/1972 | Pangman | 623/8 |
| 3,700,380 | 10/1972 | Kitrilakis | 623/66 |
| 3,852,832 | 12/1974 | McGhan | 623/8 |
| 4,413,359 | 11/1983 | Akiyama et al. | 623/11 |
| 4,455,691 | 6/1984 | Van Aken Redinger | 623/8 |
| 4,460,713 | 7/1984 | Lee | 623/8 |
| 4,531,244 | 7/1985 | Hamas | 623/8 |
| 4,648,880 | 3/1987 | Brauman | 623/8 |

OTHER PUBLICATIONS

Herman "Memg Implant" Plastic & Reconstructive Surgery vol. 73, No. 3, pp. 411–414 (Mar., 1984).
Pennisi, "Polyurethane-Covered Silicone Gel Mammary Prost. for Successful Breast Reconstruction", Aesthetic Plast. Sur. vol. 9, pp. 73–77 (1985).
Picha "Ion Beam Microtexturing of Biomed." MD & DI pp. 39–42 (1984).
Ashley "A New Type of Breast Prosthesis" J. Plastic & Reconstructive Surgery, vol. 45, No. 5 pp. 421–424 (May 1970).
Ashley "Further Studies on the Natural Y Breast Prosth" J Plastic & Reconstructive Surgery, vol. 49, No. 4 pp. 414–419 (Apr. 1972).
Capozzi, et al "Clinical Experience with Polyurethane-covered Gel Filled Mammary Prosth." J. Plastic & Reconstructive Surg. 68:512 (1981).
Marzoni, et al. "An Experimental Study of Silicone as Soft Tissue Substitute" J. Plastic & Reconstructive Surgery vol. 24, No. 6 pp. 600–608 Dec. 1959.
Lilla, et al. "Long Term Study of Reactions to Various Silicone Breast Implant in Rabbits", J. Plastic & Reconstructive Surg. vol. 57, No. 5. pp. 637–649 (May 1976).

*Primary Examiner*—David J. Isabella

[57] ABSTRACT

An improved implantable prosthetic device for use in the human body which comprises a flexible container having therein a soft gel or fluid filling and an outer plastic covering bonded or otherwise connected to the flexible container. The external surface of the outer plastic covering is rough textured, while the plastic covering itself has numerous pores or interstices. It substantially encases the flexible container. In one embodiment a barrier film is positioned between the flexible container and the outer plastic covering or between the soft gel or liquid filling and the internal of the flexible container. The outer plastic covering is made of Dacron or Teflon.

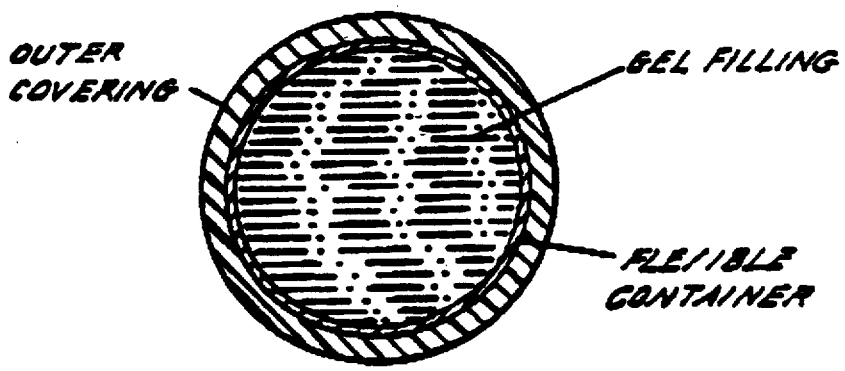

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2 and 3, dependent on an amended claim, are determined to be patentable.

1. In an implantable prosthetic device for use in a human body including a flexible container and a soft gel or liquid filling the flexible container;

the improvement which comprises providing an outer plastic covering made of rough textured silicone and bonded to the flexible container, said outer plastic [convering] *covering* having a rough textured external surface thereby providing a multiplicity of pores and/or interstices *to permit tissue ingrowth*, said outer plastic covering encases the flexible container in order to prevent the contraction of scar tissue around the prosthetic device from pulling the prosthetic device into a hard, spherical shape.

4. In a breast prosthesis comprising a flexible container approximating the shape of the human breast and a soft gel or liquid filling said container;

the improvement which comprises providing an outer, rough textured plastic covering made of rough textured silicone and which encases the flexible container and has an outer surface having a multiplicity of pores and/or interstices *to permit tissue ingrowth.*

* * * * *